(12) United States Patent
Kataja

(10) Patent No.: US 10,407,427 B2
(45) Date of Patent: Sep. 10, 2019

(54) PROCESSES FOR THE PREPARATION OF VEMURAFENIB

(71) Applicant: Fermion Oy, Espoo (FI)

(72) Inventor: Antti Kataja, Espoo (FI)

(73) Assignee: FERMION OY, Espoo (FI)

( * ) Notice: Subject to any disclaimer, the term of this patent is extended or adjusted under 35 U.S.C. 154(b) by 0 days.

(21) Appl. No.: 16/313,597

(22) PCT Filed: Jun. 30, 2017

(86) PCT No.: PCT/FI2017/000012
§ 371 (c)(1),
(2) Date: Dec. 27, 2018

(87) PCT Pub. No.: WO2018/002415
PCT Pub. Date: Jan. 4, 2018

(65) Prior Publication Data
US 2019/0194197 A1 Jun. 27, 2019

(30) Foreign Application Priority Data

Jul. 1, 2016 (FI) ..................................... 20165557
Oct. 12, 2016 (FI) ..................................... 20165778

(51) Int. Cl.
*C07D 471/04* (2006.01)

(52) U.S. Cl.
CPC .................................. *C07D 471/04* (2013.01)

(58) Field of Classification Search
CPC .................................................... C07D 471/04
USPC .......................................................... 546/113
See application file for complete search history.

(56) References Cited

FOREIGN PATENT DOCUMENTS

| WO | 2007002433 A1 | 1/2007 |
|----|---------------|--------|
| WO | 2011015522 A1 | 2/2011 |
| WO | 2012010538 A1 | 1/2012 |
| WO | 2014159353 A1 | 10/2014 |
| WO | 2015075749 A1 | 5/2015 |
| WO | 2015078424 A1 | 6/2015 |
| WO | 2016083956 A1 | 6/2016 |

OTHER PUBLICATIONS

V. Iaroshenko et al., "Design, synthesis and transformation of some heteroannulated 3-aminopyridines-purine isosteres with exocyclic nitrogen atom", Tetrahedron, 2013, pp. 1217-1228, vol. 69.
A. Mityuk et al., "An Efficient Synthesis of Fused 3-Formylpyridines and 5-Formylpyridines", Synthesis, 2010, pp. 2767-2770, No. 16, XP55407134A.

*Primary Examiner* — Patricia L Morris

(74) *Attorney, Agent, or Firm* — Buchanan Ingersoll & Rooney PC

(57) ABSTRACT

Novel processes are disclosed for manufacture of N-(3-(5-(4-chlorophenyl)-1 H-pyrrolo[2,3-b]pyridine-3-carbonyl)-2, 4-difluorophenyl)propane-1-sulfonamide (I), wherein no protection-deprotection sequences or halogenation steps are required and use of palladium catalysts is minimized.

20 Claims, No Drawings

PROCESSES FOR THE PREPARATION OF VEMURAFENIB

FIELD OF THE INVENTION

The present invention provides improved processes for the manufacture of Vemurafenib, N-(3-(5-(4-chlorophenyl)-1H-pyrrolo[2,3-b]pyridine-3-carbonyl)-2,4-difluorophenyl)propane-1-sulfonamide.

BACKGROUND OF THE INVENTION

The compound N-(3-(5-(4-chlorophenyl)-1H-pyrrolo[2,3-b]pyridine-3-carbonyl)-2,4-difluorophenyl)propane-1-sulfonamide or propane-1-sulfonic acid {3-[5-(4-chlorophenyl)-1H-pyrrolo[2,3-b]pyridine-3-carbonyl]-2,4-difluoro-phenyl}-amide (Vemurafenib) is a BRAF enzyme inhibitor effective for the treatment of diseases such as metastatic melanoma, thyroid cancers and colorectal cancers. It has the chemical formula (I) presented below.

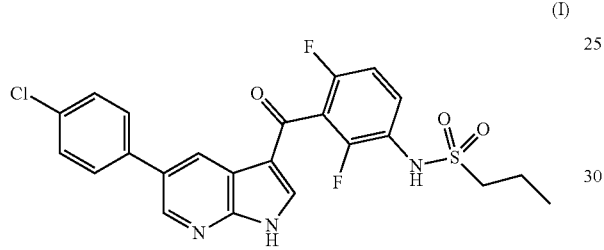

(I)

The synthesis of the compound of formula (I) has previously been described in WO 2007/002433, WO 2011/015522, and WO 2012/010538. The process described in WO 2011/015522 however suffers from the protection-deprotection strategy in the last steps which significantly decreases the overall yield, while the raw material, 1-ethoxyethene-2-boronic acid pinacol ester, used in WO 2012/010538 is an expensive reagent which is difficult to prepare.

Thus, it is desirable to provide an improved method for producing vemurafenib in high yield and purity. The utilization of new raw materials gives a process which is more cost efficient and suitable for use on large scale than the processes known in the prior art.

SUMMARY OF THE INVENTION

The present invention provides a process for the manufacture of the compound of formula (I)

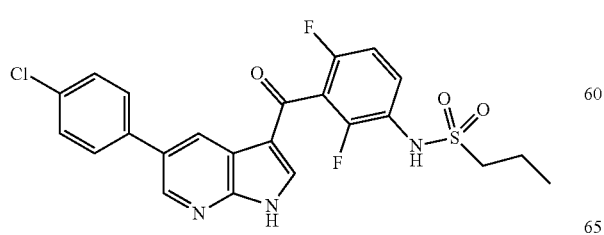

(I)

which process comprises
(a) reacting a compound of formula (III)

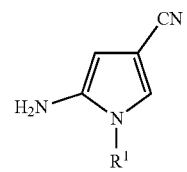

(III)

wherein $R^1$ is $C_{1-5}$ alkyl, $C_{3-6}$ cycloalkyl or optionally substituted benzyl, with either a compound of formula (IV); or a compound of formula (VI)

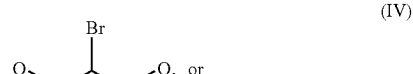

(IV)

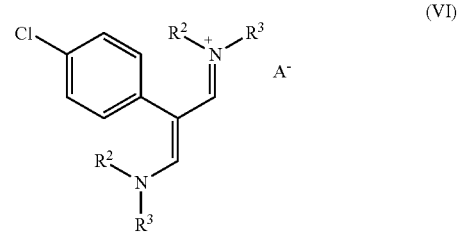

(VI)

wherein $R^2$ and $R^3$ are groups suitable for the formation of a Vilsmeier reagent and $A^-$ is a suitable non-coordinating anion, to produce a compound of formula (IX)

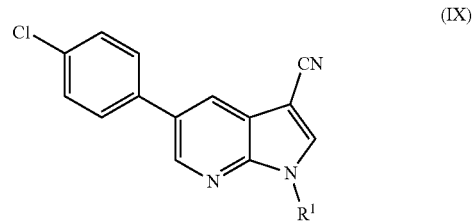

(IX)

wherein $R^1$ is as defined above, and
(b) subjecting the compound of formula (IX) to the removal of the $R^1$ group and converting the nitrile group to a carboxylic acid, and finally performing a decarboxylation to produce the compound of formula (X)

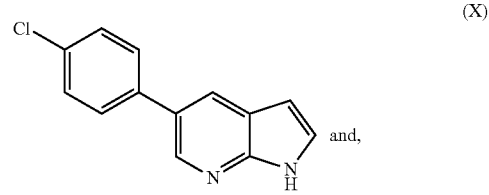 [SMILES: Clc1ccc(-c2cnc3[nH]ccc3c2)cc1]

(X)

and, (c) reacting the compound of formula (X) with 2,6-difluoro-3-(propylsulfonamido)benzoic acid to give a compound of formula (I).

In another embodiment there is provided the above described process a) to c) for the manufacture of the compound of formula (I), wherein step a) is as described above; and said compound of formula (III) is further reacted with the compound of formula (IV)

to obtain the compound of formula (VII)

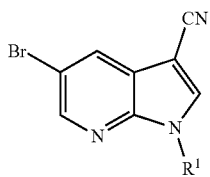

wherein $R^1$ is $C_{1-5}$ alkyl, $C_{3-6}$ cycloalkyl or optionally substituted benzyl, and subsequently treating the compound of formula (VII) with a compound of formula (VIII)

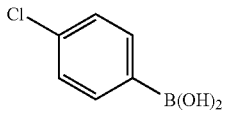

to produce a compound of formula (IX)

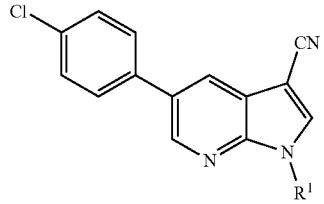

wherein $R^1$ is as defined above, and b) subjecting the compound of formula (IX) to the removal of the $R^1$ group and converting the nitrile group to a carboxylic acid, and finally performing a decarboxylation to produce the compound of formula (X)

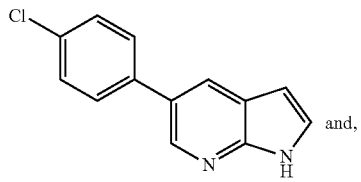

and, c) reacting the compound of formula (X) with 2,6-difluoro-3-(propylsulfonamido)benzoic acid to give a compound of formula (I).

In another embodiment according to the present invention there is provided the above described process for the manufacture of the compound of formula (I) according to steps a) to c) above, wherein step a) is as described above; and said compound of formula (III) is further reacted with the compound of formula (VI)

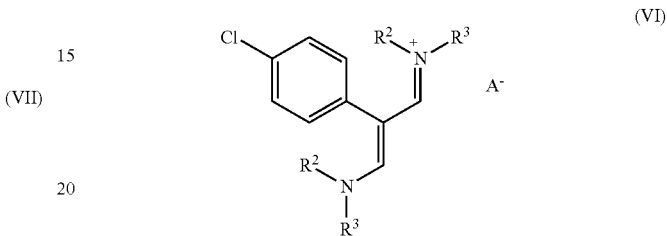

to obtain the compound of formula (IX)

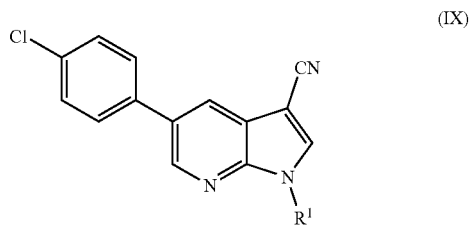

wherein $R^1$ is $C_{1-5}$ alkyl, $C_{3-6}$ cycloalkyl or optionally substituted benzyl, and (b) subjecting the compound of formula (IX) to the removal of the $R^1$ group and converting the nitrile group to a carboxylic acid, and finally performing a decarboxylation to produce the compound of formula (X)

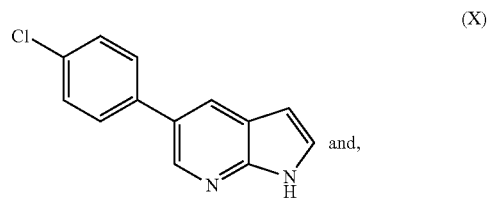 [SMILES: Clc1ccc(-c2cnc3[nH]ccc3c2)cc1]

and, (c) reacting the compound of formula (X) with 2,6-difluoro-3-(propylsulfonamido)benzoic acid to give a compound of formula (I).

In still another aspect the present invention provides processes for the manufacture of the compound of formula (I), minimizing the use of palladium catalysts and avoiding protection-deprotection sequences decreasing the overall yield. Minimizing the palladium catalyzed steps considerably decreases the risk to contaminate the product with metal residues.

DETAILED DESCRIPTION OF THE INVENTION

It was surprisingly found that significant benefits can be achieved with the processes of the invention for the manufacture of vemurafenib (I), like improved yields, reduced raw material costs and further, the process is suitable for larger industrial scale as in the present process no use of protecting groups are required and the use of palladium catalysts is significantly reduced if required at all.

The processes of the present invention can be summarized, but not limited, according to the following general reaction scheme (scheme 1) wherein, if not clearly otherwise stated, all abbreviations and expressions have the meanings well known to the person skilled in the art of organic chemistry.

Characteristic features of the invention are presented in the appended claims.

The term $C_{1-5}$ alkyl as used herein means a linear or branched, saturated hydrocarbon containing from one to five carbon-atoms, preferably from 2 to 4 carbon-atoms. The most preferred $C_{1-5}$ alkyl group according to the present invention is t-butyl.

The term $C_{3-6}$ cycloalkyl as used herein means a cyclic saturated hydrocarbon containing from three to six carbon-atoms. The most preferred $C_{3-6}$ cycloalkyl group according to the present invention is cyclohexyl.

The term "optionally substituted benzyl" as used herein refers to benzyl groups which may be substituted by 1 to 3 substituents selected from $C_{1-5}$ alkyl and $C_{1-5}$ alkoxy groups. Representative examples include methyl, ethyl, t-butyl,

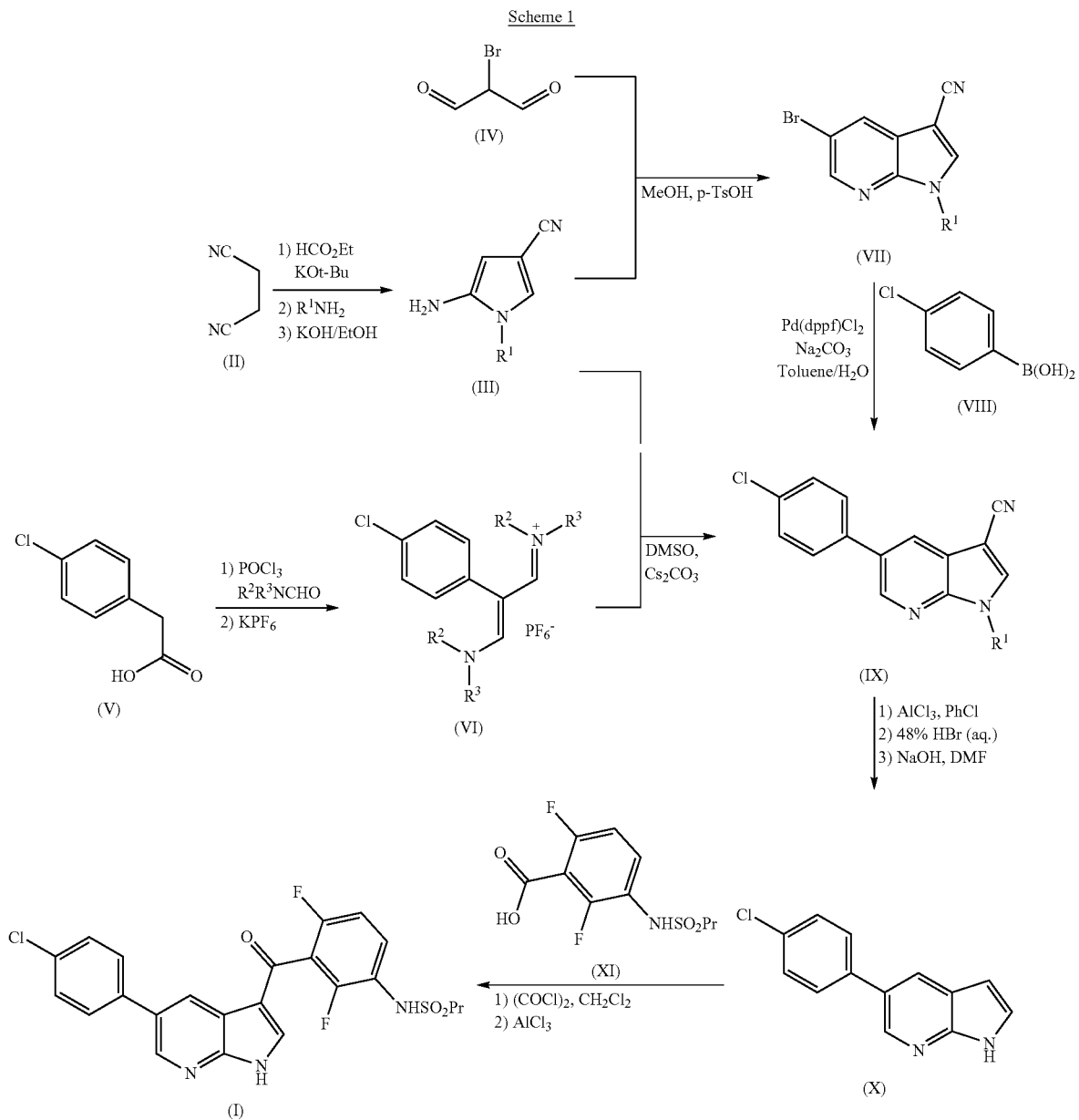

Scheme 1 methoxy, ethoxy and t-butoxy. Particularly preferred are methoxy and methyl substituents, especially methoxy group in 4-position.

The term "elevated temperature" as used herein refers to the temperature of the reaction mixture when additional heating is required. Accordingly to the present invention, elevated temperature is preferably between 30 and 150° C., more preferably 60 to 110° C.

The term "room temperature" as used herein means the ambient temperature of the place where the reaction is carried out without any additional heating or cooling. Accordingly to the present invention, room temperature is preferably between 18 and 26° C., more preferably 20 to 24° C.

The term "strong acid" as used herein means mineral acids. Preferred acids according to the present invention include HCl, HBr, HI, and $H_2SO_4$, with HCl or HBr being especially preferred.

The term "reflux" as used herein means the temperature at which the solvent or solvent system refluxes or boils at atmospheric pressure.

The term "Vilsmeier reagent" as used herein means a substituted chloroiminium ion which is formed by the reaction of a substituted amide with phosphorus oxychloride. Particularly preferred substituted amides are dialkylformamides such as N,N-dimethylformamide, N,N-diethylformamide, N,N-diisopropylformamide or N-formylpiperidine.

The term "suitable non-coordinating anion" as used herein means an anion of an alkali metal salt such as $NaPF_6$, $KPF_6$, $KBF_4$, $NaBF_4$, $NaClO_4$, $KClO_4$, preferably $KPF_6$.

In accordance with the present invention the compound of formula (III)

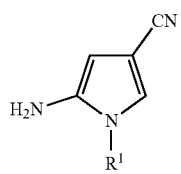
(III)

wherein $R^1$ is $C_{1-5}$ alkyl, $C_{3-6}$ cycloalkyl or optionally substituted benzyl, is reacted with the compound of formula (IV)

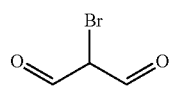
(IV)

to obtain the compound of formula (VII)

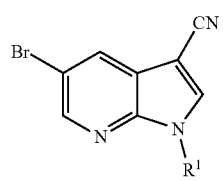
(VII)

wherein $R^1$ is as defined above.

The above described synthesis of the compound of formula (VII) is based on a cyclocondensation reaction of the pyrrole compound of formula (III) and the bromomalonaldehyde (IV). Thus, the compound of formula (III) and bromomalonaldehyde (IV) are dissolved in a suitable solvent such as methanol, ethanol, toluene or ethylene glycol. The bromomalonaldehyde of formula (IV) is typically used in a slight molar excess, e.g. in 1.0-1.5 molar equivalents per compound of formula (III). The mixture is stirred at room temperature while a suitable acid, such asp-toluenesulfonic acid, concentrated hydrochloric acid, benzenesulfonic acid, or methanesulfonic acid is added. When the reaction is carried out at elevated temperature, typically between 60 and 110° C., the reaction is typically completed within 6 hours or less. Thereafter, the reaction mixture is cooled and the solids are filtered, washed with cold solvent and dried under vacuum to obtain the compound of formula (VII).

According to present invention, the above described cyclocondensation reaction is followed by the treatment of the compound of formula (VII) with a compound of formula (VIII)

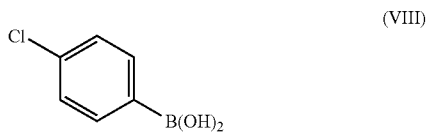
(VIII)

to obtain the compound of formula (IX)

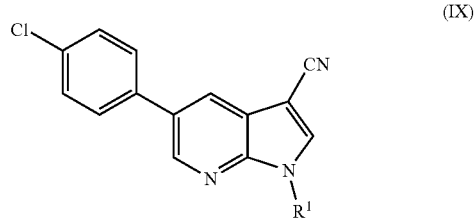
(IX)

The coupling reaction between the compound of formula (VII) and the boronic acid of formula (VIII) is carried out in the presence of a base and a palladium catalyst in a suitable solvent. Suitable solvents include, but are not limited to toluene, xylenes, acetonitrile, dioxane, dimethoxyethane (DME), and THF alone or as an aqueous mixture. Particularly preferred solvent system is a mixture of toluene and water, preferably a 1:1 mixture of toluene and water.

The base employed in the reaction depends on the nature of the solvent system but is selected from the group consisting of $Na_2CO_3$, $K_2CO_3$, NaOH, KOH, $K_3PO_4$, $Cs_2CO_3$, KOt-Bu, NaOt-Bu or mixtures thereof, most preferably $Na_2CO_3$ when a mixture of toluene and water is used as solvent.

The palladium catalyst is suitably selected from $Pd(PPh_3)_4$, $Pd(dba)_2$, $Pd_2(dba)_3$, $Pd(dppf)Cl_2 \cdot CH_2Cl_2$, $(PPh_3)_2PdCl_2$, $Pd(OAc)_2$, $PdCl_2$ or mixtures thereof. Additionally, phosphine ligands such as $PPh_3$, $P(o-tol)_3$, dppf, dppp, dppe, dppb, $PCy_3$, $P(n-Bu)_3$, $P(t-Bu)_3$, XantPhos, DPEPhos, rac-BINAP, and rac-SEGPHOS can be used in presence of Pd(II) catalysts. Preferably $Pd(dppf)Cl_2 \cdot CH_2Cl_2$ or a mixture of $Pd(OAc)_2/PPh_3$ is used.

The compound of formula (VII) and the boronic acid of formula (VIII) together with the sodium carbonate are added to the mixture of toluene and water. The boronic acid is typically used in molar excess, e.g. in 1.2-1.5 molar equivalents per compound of formula (VII). The suspension is preferably degassed with nitrogen gas, after which the palladium catalyst is added. The mixture is again degassed, and then heated to reflux. The reaction is typically completed after about 5 hours, after which the mixture is cooled to room temperature and the layers are allowed to separate. The organic layer is filtered through Celite and concentrated to give the crude product, which is triturated with petroleum ether followed by slurrying at room temperature in an ethyl acetate/petrol ether mixture, preferably a mixture of 10% ethyl acetate in petrol ether. The solids are filtered and dried under vacuum to obtain the compound of formula (IX).

In another preferred embodiment according to the present invention the compound of formula (IX) is obtained by reacting the compound of formula (III)

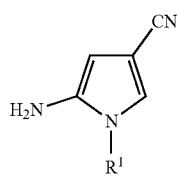
(III)

wherein $R^1$ is $C_{1-5}$ alkyl, $C_{3-6}$ cycloalkyl or optionally substituted benzyl, with the compound of formula (VI)

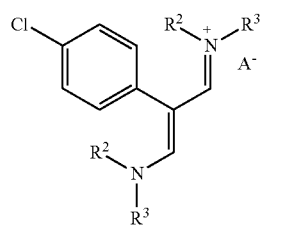
(VI)

wherein $R^2$ and $R^3$ are groups suitable for the formation of a Vilsmeier reagent and $A^-$ is a suitable non-coordinating anion.

The above reaction is based on cyclocondensation of the pyrrole compound of formula (III) and the vinamidinium salt of formula (VI) under alkaline conditions, suitably using $K_2CO_3$, $Na_2CO_3$, $Cs_2CO_3$, NaOH, NaOMe or KOH as base. The base is typically used in molar excess e.g. in 1.1-6 molar equivalents per compound of formula (III). The vinamidinium salt of formula (VI) is typically used in molar excess, e.g. in 1.1-2 molar equivalents per compound of formula (III). The reaction is carried out in a suitable solvent, such as DMSO, DMF, toluene, $CH_3CN$, MeOH or NMP, under nitrogen atmosphere. The reagents are suitably added at room temperature and the mixture is heated to about 65-120° C. The reaction is typically completed within about 16 hours. The reaction can be quenched with addition of cold water. The resulting compound of formula (IX) can be isolated by filtration and slurrying the crude compound in a suitable solvent or the compound of formula (IX) can be isolated by extraction or the crude compound can be forwarded directly to the next step.

Compounds of formula (III) can be prepared using the methods known in the art.

For example, compound of formula (III) can suitably be prepared by reacting a compound of formula (II)

(II)

with ethyl formate and a compound of formula $R^1$—$NH_2$. Suitable $R^1$ groups include, but are not limited to, $C_{1-5}$ alkyl, $C_{3-6}$ cycloalkyl, $C_{3-5}$ alkenyl or optionally substituted benzyl, or sulfonyl, or carbonyl. Thus, to a cold suspension of potassium tert-butoxide in toluene is added a solution of compound of formula (II) and ethyl formate in toluene keeping the temperature between −10 and 10° C. The mixture is warmed to room temperature and stirred for about 2 hours. To the mixture is added a compound of formula $R^1$—$NH_2$ and acetic acid and the mixture is heated to about 85° C. The reaction is typically completed within 2-3 hours. The mixture is cooled to 50-55° C., solid potassium hydroxide is added, and stirring continued at this temperature for 16 hours. When the reaction is completed the mixture is concentrated and water is added after which the resulting slurry is filtered, washed and dried to obtain the compound of formula (III).

Alternatively, the reaction between the compound of formula (II), ethyl formate and the compound of formula $R^1$—$NH_2$ can be carried out in the presence of a base such NaOMe, NaOEt, NaOt-Bu, LiHMDS, NaHMDS or KHMDS, in an aprotic solvent which is compatible with strong bases, such as xylene, CPME, MTBE or THF.

Compounds of formula (VI) can be prepared using the methods known in the art.

For example, compound of formula (VI) can be suitably prepared by reacting a compound of formula (V)

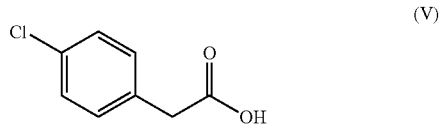 [SMILES: O=C(O)Cc1ccc(Cl)cc1]
(V)

with a compound of formula $R^2R^3NCHO$, wherein $R^2$ and $R^3$, independently, are methyl, ethyl, isopropyl, or together with the nitrogen atoms to which they are attached form a piperidine ring. A compound of formula (VI) wherein $R^2$ and $R^3$ are methyl is suitably prepared by slowly adding phosphorus oxychloride to an anhydrous solution of DMF and compound of formula (V) at temperatures between 10° C. and 70° C. The mixture is further heated to about 70-85° C. and stirred at this temperature for about 2-4 hours. When the reaction is complete the reaction mass is cooled down to room temperature and slowly added into a cooled aqueous mixture or solution of alkali metal salt of a non-coordinating anion such as $NaPF_6$, $KPF_6$, $KBF_4$, $NaBF_4$, $NaClO_4$, $KClO_4$, or a combination of corresponding acids and alkali metal hydroxides, is added to the mixture, preferably $KPF_6$. After the addition is completed the mixture is further stirred for about 30 minutes. The amount of alkali metal salt used (e.g. $KPF_6$) is suitably between about 0.5-2.5 molar equivalents, more typically between 1.0-1.5 molar equivalents, per compound of formula (V). The precipitate formed during the addition is filtered, washed with cold water, alcohol and dried to obtain the compound of formula (VI).

According to one embodiment of the invention, particularly suitable compounds of formula (III), (VII), and (IX) are those wherein $R^1$ is t-butyl, cyclohexyl, or 4-methoxybenzyl. Particularly preferred compounds of formula (III), (VII), and (IX) are those wherein $R^1$ is t-butyl.

According to one embodiment the compound of formula (IX) is subjected to removal of the $R^1$ group. The conditions for the removal will depend on the identity of the $R^1$ group. For example, when $R^1$ is t-butyl, the compound of formula (IX) can be treated with aluminium trichloride to remove the t-butyl group. Thus, anhydrous aluminium trichloride is added to chlorobenzene or toluene, followed by compound of formula (IX). After stirring at reflux under nitrogen atmosphere for about 10 hours the reaction is quenched by the addition of cold water and alcohol and stirred at temperatures between 25-80° C. for about 30-120 min. The precipitated material is filtered, washed and dried. After which the nitrile group is hydrolysed by treating it with a strong acid, suitably hydrochloric or hydrobromic acid, to produce the corresponding carboxylic acid as hydrochloride salt or as hydrobromide salt. The reaction is typically completed after stirring at reflux for about 24 hours. The reaction mixture is cooled down and the resulting carboxylic acid is filtered, washed and dried. Alternatively, the removal of $R^1$ and nitrile hydrolysis can be performed in one-pot operation. First the $R^1$ is cleaved with the aid of 95-100 w-% sulfuric acid at temperatures between 90-130° C. for about 3 hours. After complete removal of $R^1$-group, the reaction mixture is diluted with water and the mixture is stirred at temperatures between 90-130° C. for about 24 hours. After cooling and filtration the corresponding carboxylic acid is obtained as hydrogen sulfate.

Finally, the compound of formula (X)

(X)

is obtained by decarboxylation under basic conditions. The base catalysed decarboxylation reaction is carried out in DMF at about 95° C., by adding a solution of sodium hydroxide in water and stirring for about 6 hours. When the reaction is completed the reaction mixture is cooled to room temperature and poured into cold water and the slurry is further stirred for about 30 minutes. The precipitated compound of formula (X) is filtered and dried.

Alternatively, the decarboxylation reaction to form the compound of formula (X) can be carried out in an organic solvent such as DMSO or toluene, in the presence of a base such as KOH, $K_2CO_3$, $Na_2CO_3$, DIPEA or $Et_3N$, or alternatively the decarboxylation can be carried out in 48 w-% NaOH-solution without an organic solvent.

Vemurafenib is obtained from the compound of formula (X) by reacting it with 2,6-difluoro-3-(propylsulfonamido) benzoic acid. The Reaction is suitably carried out under Friedel-Crafts acylation conditions, like described in WO 2012/010538.

The present invention is further illustrated with the following non-limiting examples.

EXAMPLES

Example 1. Preparation of 5-amino-1-(tert-butyl)-1H-pyrrole-3-carbonitrile

To a 1 L three-necked flask equipped with a mechanical stirrer and nitrogen inlet was loaded toluene (350 mL) and potassium t-butoxide (72.0 g, 0.64 mol) at 25° C. while stirring. The suspension was cooled to 0-5° C. A solution of succinonitrile (50.0 g, 0.62 mol) and ethyl formate (54.64 g, 0.74 mol) in toluene (150 mL) was added slowly, maintaining internal temperature at 0-5° C. The mixture was let warm to 24° C. and stirred for 2 hours. To the mixture were added tert-butylamine (46.0 g, 0.63 mol) and AcOH (44.0 g, 0.73 mol). The internal temperature of the mixture rose to 40° C. upon this addition. The mixture was heated to 85° C. and stirred for 2.5 hours, and the reaction progress was monitored by GC. Upon completion, the mixture was cooled to 50-55° C. and potassium hydroxide (50 g, 0.89 mol) was added to the reaction mass. The mixture was stirred at this temperature for 16 hours, until GC showed completion of reaction. The solvents were evaporated and the remaining mass slurried with $H_2O$ (500 mL). The mixture was filtered and the filter cake washed with $H_2O$ (250 mL) and dried under vacuum at 50-55° C. to give the title compound as a dark brown solid (68 g, 67%). $^1$H NMR (300 MHz, DMSO-$d_6$, 2.50 ppm): δ 7.15 (d, J=2.3 Hz, 1H), 5.55 (d, J=2.3 Hz, 1H), 4.45 (s, 2H), 1.53 (s, 9H). $^{13}$C NMR (75 MHz, DMSO-$d_6$, 40.0 ppm): δ 140.07, 121.46, 118.47, 95.99, 87.58, 29.57.

Example 2. Preparation of 5-bromo-1-(tert-butyl)-1H-pyrrolo[2,3-b]pyridine-3-carbonitrile To a 500 mL flask equipped with a mechanical stirrer, a reflux condenser and a nitrogen inlet was loaded anhydrous MeOH (250 mL) followed by 5-amino-1-(tert-butyl)-1H-pyrrole-3-carbonitrile (50 g, 0.31 mol) and bromomalonaldehyde (50.8 g, 0.34 mol), and the mixture was stirred at room temperature. To the solution was added p-toluenesulfonic acid (11.65 g, 0.061 mol), and the reaction was heated to 60° C. and stirred for 6 hours. Upon completion, the reaction mass was cooled to 0-5° C. The solids were filtered, washed with cold MeOH and dried under vacuum to give the title compound as a white solid (40 g, 47%). $^1$H NMR (300 MHz, DMSO-$d_6$, 2.50 ppm): δ 8.58 (s, 1H), 8.52 (d, J=2.3 Hz, 1H), 8.37 (d, J=2.3 Hz, 1H), 1.74 (s, 9H). $^{13}$C NMR (75 MHz, DMSO, 40.0 ppm): δ 145.37, 144.62, 137.89, 130.10, 122.74, 115.25, 113.90, 81.90, 59.27, 28.93.

Example 3. Preparation of 5-(4-chlorophenyl)-1-(tert-butyl)-1H-pyrrolo[2,3-b]pyridine-3-carbonitrile To a 500 mL flask equipped with mechanical stirrer, reflux condenser and a nitrogen inlet were loaded toluene (228 mL) and water (228 mL) followed by 5-bromo-1-(tert-butyl)-1H-pyrrolo[2,3-b]pyridine-3-carbonitrile (38 g, 0.14 mol), 4-chlorophenylboronic acid (30 g, 0.19 mol) and sodium carbonate (31.8 g, 0.30 mol). The suspension was degassed with nitrogen gas for 1 hour, after which to the mixture was added Pd(dppf)$Cl_2$.$CH_2Cl_2$ complex (0.99 g, 0.0012 mol). The mixture was again degassed for 1 hour, and then heated to 85° C. for 5 hours. Upon completion the mixture was cooled to room temperature and the layers were allowed to separate. The organic layer was filtered through Celite and concentrated to give the crude product, which was triturated with petroleum ether (190 mL) followed by slurrying in 10% EtOAc in petrol ether at room temperature. The solids were filtered and dried under vacuum to give the title compound as a pale brown solid (37 g, 87%). $^1$H NMR (300 MHz, DMSO-$d_6$, 2.50 ppm): δ 8.74 (d, J=2.2 Hz, 1H), 8.55 (s, 1H), 8.33 (d, J=2.2 Hz, 1H), 7.84 (d, J=8.5 Hz, 2H), 7.54 (d, J=8.5 Hz, 2H), 1.79 (s, 9H). $^{13}$C NMR (75 MHz, DMSO-$d_6$, 40.0 ppm): δ 146.63, 143.22, 137.18, 136.93, 133.11, 129.54, 129.47, 125.85, 121.32, 115.87, 82.51, 59.06, 29.09.

Example 4. Preparation of N-(2-(4-chlorophenyl)-3-(dimethylamino)allylidene)-N-methylmethanaminium hexafluorophosphate Anhydrous DMF (227 mL) was loaded in a 500 mL flask and cooled to 0° C. Phopshorus oxychloride (179.6 g, 1.17 mol) was added slowly while stirring the mixture. The reaction mixture was warmed to 25° C. and stirred for 1.5 h. 4-Chlorophenylacetic acid (100 g, 0.59 mol) was added to the mixture at 25° C. The reaction was heated to 85° C. and stirred at this temperature under nitrogen atmosphere, until HPLC shows complete consumption of starting material. The reaction mass was then cooled to 25° C. and added slowly into cold water (1 L) while maintaining an internal temperature of 0-3° C. After the addition is completed, the mixture is stirred for 30 minutes at 0-5° C. A solution of $KPF_6$ (130 g, 0.70 mol) in $H_2O$ (500 mL) was added slowly at 0-5° C. and the mixture was stirred for 30 minutes at this temperature. The precipitate was filtered and the cake washed with cold water (500 mL). The filtered product was dried under vacuum at 50° C. to give 205 g (91.3%) of the title compound. $^1$H NMR (300 MHz, DMSO-$d_6$, 2.50 ppm): δ 7.72 (s, 2H), 7.50 (d, J=8.4 Hz, 2H), 7.34 (d, J=8.4 Hz, 2H), 3.25 (s, 6H), 2.45 (s, 6H). $^{13}$C NMR (75 MHz, CDCl$_3$) δ 163.83, 135.04, 133.47, 130.82, 128.74, 104.20, 48.94, 39.63.

Example 5. Preparation of N-(2-(4-chlorophenyl)-3-(dimethylamino)allylidene)-N-methylmethanaminium hexafluorophosphate 4-Chlorophenylacetic acid (70 g, 0.41 mol) was charged to a 1 L reactor followed by anhydrous DMF (275 mL, 3.55 mol) and the solution was heated to 70° C. Phosphorus oxychloride (77 mL, 0.83 mol) was added to the heated solution during four hours at 70° C. After the addition was complete the solution was further heated at 70° C. for four hours. After the reaction was complete the mixture was allowed to cool to room temperature and transferred into a dropping funnel. In a separate reactor potassium hexafluorophosphate (91 g, 0.49 mol) was slurried in water (700 mL) and cooled to 10° C. The reaction mixture was added to the $KPF_6$-solution during one hour at a temperature below 20° C. The mixture was allowed to warm at room temperature and further stirred for one hour. The compound of formula (VI) was filtered and washed with water (2×350 mL) and EtOH (350 mL). The product was dried in vacuum oven at 50° C. for 16 hours to give 145 g (92.2%) of the titel product as pale yellow solid. $^1$H NMR (300 MHz, DMSO-$d_6$, 2.50 ppm): δ 7.72 (s, 2H), 7.50 (d, J=8.4 Hz, 2H), 7.34 (d, J=8.4 Hz, 2H), 3.25 (s, 6H), 2.45 (s, 6H). $^{13}$C NMR (75 MHz, CDCl$_3$) δ 163.83, 135.04, 133.47, 130.82, 128.74, 104.20, 48.94, 39.63.

Example 6. Preparation of N-(2-(4-chlorophenyl)-3-(dimethylamino)allylidene)-N-methylmethanaminium tetrafluoroborate 4-Chlorophenylacetic acid (10 g, 68.6 mmol) and anhydrous DMF (33 mL, 426 mmol) were charged to a round-bottomed flask and the solution was cooled under nitrogen between 10-15° C. Phosphorus oxychloride (11 mL, 118 mmol) was added to the cooled solution and the temperature was kept under 35° C. during the addition. The mixture was allowed to stir at room temperature for 45 minutes and then heated to 85° C. The heating was continued between 80° C.-85° C. for two hours. After the reaction was complete the mixture was allowed to cool to room temperature and transferred into a dropping funnel. In a separate flask sodium tetrafluoroborate (12.9 g, 117 mmol) was slurried in water (80 mL) and cooled to 0-5° C. The reaction mixture was added to the $NaBF_4$-solution during 30 minutes. The mixture was further stirred at 5° C. for 60 minutes and filtered. The product was washed with water (20 mL) and i-PrOH (20 mL). The product was dried in vacuum oven at 50° C. for 16 hours to give 11.9 g (62.4%) of the vinamidinium salt as a yellow solid. $^1$H NMR (300 MHz, DMSO-$d_6$, 2.50 ppm): δ 7.72 (s, 2H), 7.50 (d, J=8.4 Hz, 2H), 7.34 (d, J=8.4 Hz, 2H), 3.25 (s, 6H), 2.45 (s, 6H). $^{13}$C NMR (75 MHz, CDCl$_3$) δ 163.83, 135.04, 133.47, 130.82, 128.74, 104.20, 48.94, 39.63.

Example 7. Preparation of 5-(4-chlorophenyl)-1-(tert-butyl)-1H-pyrrolo[2,3-b]pyridine-3-carbonitrile Into a 1 L flask equipped with a mechanical stirrer and a reflux condenser were loaded anhydrous DMSO (300 mL), 5-amino-1-(tert-butyl)-1H-pyrrole-3-carbonitrile (30.0 g, 0.184 mol) and N-(2-(4-chlorophenyl)-3-(dimethylamino)allylidene)-N-methylmethanaminium hexafluorofosfate (112.5 g, 0.29 mol) at room temperature, followed by $Cs_2CO_3$ (359.3 g, 1.10 mol). The mixture was heated to 80° C. and stirred for 16 hours under nitrogen atmosphere. After completion, the mixture was cooled to 25° C. and quenched with $H_2O$ (300 mL) upon which a precipitate was formed. The solids were filtered and slurried in MeOH for 30 minutes at room temperature, then filtered and dried. The solid was dissolved in refluxing EtOAc (300 mL), and slowly cooled to room temperature and filtered. The filter cake was washed with EtOAc. The filtrate was concentrated, and solvents were swapped to heptane. When all EtOAc was removed, the remaining precipitate was stirred in heptane for 30 minutes at room temperature. The precipitate was filtered, washed with heptane and dried under vacuum to give the title compound (43.6 g, 76.6%). $^1$H NMR (300 MHz, DMSO-$d_6$, 2.50 ppm): δ 8.74 (d, J=2.2 Hz, 1H), 8.55 (s, 1H), 8.33 (d, J=2.2 Hz, 1H), 7.84 (d, J=8.5 Hz, 2H), 7.54 (d, J=8.5 Hz, 2H), 1.79 (s, 9H). $^{13}$C NMR (75 MHz, DMSO-$d_6$, 40.0 ppm): δ 146.63, 143.22, 137.18, 136.93, 133.11, 129.54, 129.47, 125.85, 121.32, 115.87, 82.51, 59.06, 29.09.

Example 8. Preparation of 5-(4-chlorophenyl)-1-(tert-butyl)-1H-pyrrolo[2,3-b]pyridine-3-carbonitrile Into a round-bottomed flask equipped with a mechanical stirrer and a reflux condenser were loaded 5-amino-1-(tert-butyl)-1H-pyrrole-3-carbonitrile (6.0 g, 36.8 mmol), N-(2-(4-chlorophenyl)-3-(dimethylamino)allylidene)-N-methyl-methanaminium hexafluorofosfate (15.60 g, 40.8 mmol), $CH_3CN$ (60 mL) and $Cs_2CO_3$ (18.0 g, 55.2 mmol). The mixture was heated to 80° C. and stirred for 6 hours under nitrogen atmosphere. HPLC indicated the completion of the reaction. Water (60 mL) and toluene (60 mL) were added to the reaction mixture and the phases were separated hot. The organic-phase was washed with water (60 mL, hot) and the phases were separated. The toluene phase was concentrated to 30 mL and cooled to 4° C. during four hours. The formed precipitation was filtered and washed with MeOH (2×20 mL). The product was dried in vacuum oven for 16 hours yielding 7.6 g (66.5%) of the title compound as light yellow solid. $^1$H NMR (300 MHz, DMSO-$d_6$, 2.50 ppm): δ 8.74 (d, J=2.2 Hz, 1H), 8.55 (s, 1H), 8.33 (d, J=2.2 Hz, 1H), 7.84 (d, J=8.5 Hz, 2H), 7.54 (d, J=8.5 Hz, 2H), 1.79 (s, 9H). $^{13}$C NMR (75 MHz, DMSO-d$_6$, 40.0 ppm): δ 146.63, 143.22, 137.18, 136.93, 133.11, 129.54, 129.47, 125.85, 121.32, 115.87, 82.51, 59.06, 29.09.

Example 9. Preparation of 5-(4-chlorophenyl)-1-(tert-butyl)-1H-pyrrolo[2,3-b]pyridine-3-carbonitrile Into a round-bottomed flask equipped with a mechanical stirrer and a reflux condenser were loaded 5-amino-1-(tert-butyl)-1H-pyrrole-3-carbonitrile (2.0 g, 12.25 mmol), N-(2-(4-chlorophenyl)-3-(dimethylamino)allylidene)-N-methyl-methanaminium tetrafluoroborate (4.4 g, 13.56 mmol), DMSO (20 mL) and Cs$_2$CO$_3$ (6.0 g, 18.42 mmol). The mixture was heated to 80° C. and stirred for 1.5 hours under nitrogen atmosphere. HPLC indicated the completion of the reaction.

Water (20 mL) and toluene (20 mL) were added to the reaction mixture and the phases were separated hot. The organic-phase was washed with water (20 mL, hot) and the phases were separated. The toluene phase was concentrated to 10 mL and cooled to 4° C. during four hours. The formed precipitation was filtered and washed with MeOH (2×6 mL). The product was dried in vacuum oven for 16 hours yielding 2.7 g (71.05%) of the title compound as light yellow solid. $^1$H NMR (300 MHz, DMSO-d$_6$, 2.50 ppm): δ 8.74 (d, J=2.2 Hz, 1H), 8.55 (s, 1H), 8.33 (d, J=2.2 Hz, 1H), 7.84 (d, J=8.5 Hz, 2H), 7.54 (d, J=8.5 Hz, 2H), 1.79 (s, 9H). $^{13}$C NMR (75 MHz, DMSO-d$_6$, 40.0 ppm): δ 146.63, 143.22, 137.18, 136.93, 133.11, 129.54, 129.47, 125.85, 121.32, 115.87, 82.51, 59.06, 29.09.

Example 10. Preparation of 5-(4-chlorophenyl)-1-(tert-butyl)-1H-pyrrolo[2,3-b]pyridine-3-carbonitrile Into a round-bottomed flask equipped with a mechanical stirrer and a reflux condenser were loaded 5-amino-1-(tert-butyl)-1H-pyrrole-3-carbonitrile (20.0 g, 123 mmol), N-(2-(4-chlorophenyl)-3-(dimethylamino)allylidene)-N-methyl-methanaminium hexafluorofosfate (52.0 g, 136 mmol), MeOH (200 mL) and 25 w-% NaOMe/MeOH— solution (42.0 mL, 184 mmol). The mixture was heated to reflux and stirred for 26 hours under nitrogen atmosphere. The reaction mixture was allowed to cool to room temperature and treated with water (100 mL). The mixture was stirred at room temperature for two hours and then cooled to 0° C. The product was filtered and washed with MeOH (2×60 mL). After drying in vacuum oven at 50° C. for 16 hours the title product was obtained as a light yellow solid. The isolated yield was 29.06 g (76.6%). $^1$H NMR (300 MHz, DMSO-d$_6$, 2.50 ppm): δ 8.74 (d, J=2.2 Hz, 1H), 8.55 (s, 1H), 8.33 (d, J=2.2 Hz, 1H), 7.84 (d, J=8.5 Hz, 2H), 7.54 (d, J=8.5 Hz, 2H), 1.79 (s, 9H). $^{13}$C NMR (75 MHz, DMSO-d$_6$, 40.0 ppm): δ 146.63, 143.22, 137.18, 136.93, 133.11, 129.54, 129.47, 125.85, 121.32, 115.87, 82.51, 59.06, 29.09.

Example 11. Preparation of 5-(4-chlorophenyl)-1-(tert-butyl)-1H-pyrrolo[2,3-b]pyridine-3-carbonitrile Into a round-bottomed flask equipped with a mechanical stirrer and a reflux condenser were loaded 5-amino-1-(tert-butyl)-1H-pyrrole-3-carbonitrile (110.0 g, 674 mmol), N-(2-(4-chlorophenyl)-3-(dimethylamino)allylidene)-N-methyl-methanaminium hexafluorofosfate (286.0 g, 747 mmol), DMSO (800 mL) and 25 w-% NaOMe/MeOH— solution (231.0 mL, 1011 mmol). The mixture was heated to 100° C. and stirred for one hour under nitrogen atmosphere. The reaction mixture was allowed to cool to room temperature and treated with water (550 mL). The mixture was stirred at room temperature for one hour and then cooled to 0° C. and further stirred for one hour. The product was filtered and washed with water (2×200 mL) and MeOH (3×200 mL). After drying in vacuum oven at 50° C. for 16 hours the title product was obtained as a yellow solid. The isolated yield was 194.02 g (92.9%). $^1$H NMR (300 MHz, DMSO-d$_6$, 2.50 ppm): δ 8.74 (d, J=2.2 Hz, 1H), 8.55 (s, 1H), 8.33 (d, J=2.2 Hz, 1H), 7.84 (d, J=8.5 Hz, 2H), 7.54 (d, J=8.5 Hz, 2H), 1.79 (s, 9H). $^{13}$C NMR (75 MHz, DMSO-d$_6$, 40.0 ppm): δ 146.63, 143.22, 137.18, 136.93, 133.11, 129.54, 129.47, 125.85, 121.32, 115.87, 82.51, 59.06, 29.09.

Example 12. Preparation of 5-(4-chlorophenyl)-1H-pyrrolo[2,3-b]pyridine-3-carbonitrile To a 1 L flask equipped with mechanical stirrer, reflux condenser & nitrogen inlet was loaded chlorobenzene (400 mL) and anhydrous AlCl$_3$ (52 g, 0.39 mol), followed by 1-(tert-butyl)-5-(4-chlorophenyl)-1H-pyrrolo[2,3-b]pyridine-3-carbonitrile (40.0 g, 0.13 mol). The reaction mass was heated to 100° C. under nitrogen atmosphere and stirred overnight. Upon completion, the reaction was cooled to room temperature and quenched with cold H$_2$O (450 mL) and stirred at room temperature for 30 minutes. The solids were filtered and washed with cold H$_2$O. The crude product was purified by slurrying in petrol ether at room temperature. Filtration and drying under vacuum gave the title compound as a pale pink solid (32 g, 99%). $^1$H NMR (300 MHz, DMSO-d$_6$, 2.50 ppm): δ 12.93 (s, 1H), 8.69 (d, J=2.2 Hz, 1H), 8.48 (s, 1H), 8.34 (d, J=2.2 Hz, 1H), 7.81 (d, J=8.5 Hz, 2H), 7.52 (d, J=8.5 Hz, 2H). $^{13}$C NMR (75 MHz, DMSO-d$_6$, 40.0 ppm): δ 147.53, 144.37, 137.13, 136.90, 132.97, 129.71, 129.41, 128.63, 125.66, 119.47, 115.93, 84.20.

Example 13. Preparation of 5-(4-chlorophenyl)-1H-pyrrolo[2,3-b]pyridine-3-carbonitrile To a round-bottomed flask equipped with mechanical stirrer, reflux condenser & nitrogen inlet was loaded chlorobenzene (100 mL) and anhydrous AlCl$_3$ (12.9 g, 97 mmol), followed by 1-(tert-butyl)-5-(4-chlorophenyl)-1H-pyrrolo[2,3-b]pyridine-3-carbonitrile (10.0 g, 32.3 mmol). The reaction mass was heated to 100° C. under nitrogen atmosphere and stirred for nine hours. Upon completion, the reaction was cooled to 5° C. and quenched with H$_2$O (50 mL) and MeOH (30 mL). The mixture was heated to 80° C. and stirred for 60 to 120 minutes. The solids were filtered and washed with H$_2$O (3×50 mL) and MeOH (2×30 mL). After drying in vacuum oven at 50° C. for 16 hours 7.8 g (95%) of the title product was obtained. $^1$H NMR (300 MHz, DMSO-d$_6$, 2.50 ppm): δ 8.74 (d, J=2.2 Hz, 1H), 8.55 (s, 1H), 8.33 (d, J=2.2 Hz, 1H), 7.84 (d, J=8.5 Hz, 2H), 7.54 (d, J=8.5 Hz, 2H), 1.79 (s, 9H). $^{13}$C NMR (75 MHz, DMSO-d$_6$, 40.0 ppm): δ 146.63, 143.22, 137.18, 136.93, 133.11, 129.54, 129.47, 125.85, 121.32, 115.87, 82.51, 59.06, 29.09.

Example 14. Preparation of 5-(4-chlorophenyl)-1H-pyrrolo[2,3-b]pyridine-3-carbonitrile To a round-bottomed flask equipped with mechanical stirrer, reflux condenser & nitrogen inlet was loaded toluene (100 mL) and anhydrous AlCl$_3$ (12.9 g, 97 mmol), followed by 1-(tert-butyl)-5-(4-chlorophenyl)-1H-pyrrolo[2,3-b]pyridine-3-carbonitrile (10.0 g, 32.3 mmol). The reaction mass was heated to 110° C. under nitrogen atmosphere and stirred for four hours. Upon completion, the reaction was cooled to 5° C. and quenched with H$_2$O (50 mL) and MeOH (30 mL). The mixture was heated to 80° C. and stirred for 60 to 120 minutes. The solids were filtered and washed with H$_2$O (3×50 mL) and MeOH (2×30 mL). After drying in vacuum oven at 50° C. for 16 hours 8.03 g (98%) of the title product was obtained. $^1$H NMR (300 MHz, DMSO-d$_6$, 2.50 ppm): δ 8.74 (d, J=2.2 Hz, 1H), 8.55 (s, 1H), 8.33 (d, J=2.2 Hz, 1H), 7.84 (d, J=8.5 Hz, 2H), 7.54 (d, J=8.5 Hz, 2H), 1.79 (s, 9H). $^{13}$C NMR (75 MHz, DMSO-d$_6$, 40.0 ppm): δ 146.63, 143.22, 137.18, 136.93, 133.11, 129.54, 129.47, 125.85, 121.32, 115.87, 82.51, 59.06, 29.09.

Example 15. Preparation of 5-(4-chlorophenyl)-1H-pyrrolo[2,3-b]pyridine-3-carboxylic acid hydrobromide salt To a 1 L flask equipped with a mechanical stirrer and a reflux condenser was loaded hydrobromic acid (480 mL, 48% in H$_2$O) followed by 5-(4-chlorophenyl)-1H-pyrrolo[2,3-b]pyridine-3-carbonitrile (32.0 g, 0.126 mol). The resulting suspension was heated to 100° C. for 24 hours, then cooled to room temperature. The reaction mass was diluted with 320 mL H$_2$O. The solids were filtered and washed with water and taken to next step without further purification (33 g, 74%). $^1$H NMR (300 MHz, DMSO-d$_6$, 2.50 ppm): δ 12.60 (s, 1H), 8.62 (d, J=2.3 Hz, 1H), 8.50 (d, J=2.2 Hz, 1H), 8.20 (d, J=2.4 Hz, 1H), 7.75 (d, J=8.6 Hz, 2H), 7.55 (d, J=8.5 Hz, 2H). $^{13}$C NMR (75 MHz, DMSO-d$_6$, 40.0 ppm): δ 165.70, 148.50, 142.78, 137.80, 134.17, 132.71, 129.49, 129.33, 129.28, 127.32, 119.01, 107.15.

Example 16. Preparation of 5-(4-chlorophenyl)-1H-pyrrolo[2,3-b]pyridine-3-carboxylic acid hydrogen sulfate To a round-bottomed flask equipped with mechanical stirrer, reflux condenser & nitrogen inlet was loaded sulfuric acid (95-98 w-%, 100 mL) and 1-(tert-butyl)-5-(4-chlorophenyl)-1H-pyrrolo[2,3-b]pyridine-3-carbonitrile (20.0 g, 64.6 mmol). The reaction mass was heated to 100° C. under nitrogen atmosphere and stirred for three hours. Upon completion, the reaction mixture was allowed to cool to room temperature and transferred to dropping funnel. The mixture was added dropwise to water (100 mL) during 40 minutes. The resulting mixture was heated to 100° C. and stirred for 24 hours. Water (50 mL) was added to the reaction and the mixture was allowed to cool at room temperature during two hours. The solids were filtered and washed with EtOH (2×50 mL). After drying in vacuum oven at 50° C. for 16 hours 20.66 g (86%) of the title product was obtained. $^1$H NMR (300 MHz, DMSO-d$_6$, 2.50 ppm): δ 12.60 (s, 1H), 8.62 (d, J=2.3 Hz, 1H), 8.50 (d, J=2.2 Hz, 1H), 8.20 (d, J=2.4 Hz, 1H), 7.75 (d, J=8.6 Hz, 2H), 7.55 (d, J=8.5 Hz, 2H). $^{13}$C NMR (75 MHz, DMSO-d$_6$, 40.0 ppm): δ 165.70, 148.50, 142.78, 137.80, 134.17, 132.71, 129.49, 129.33, 129.28, 127.32, 119.01, 107.15.

Example 17. Preparation of 5-(4-chlorophenyl)-1H-pyrrolo[2,3-b]pyridine

To a 500 mL flask equipped with a mechanical stirrer and a reflux condenser was loaded N,N-dimethylformamide (160 mL) followed by 5-(4-chlorophenyl)-1H-pyrrolo[2,3-b]pyridine-3-carboxylic acid (35.0 g, 0.12 mol, wet material). To the mixture was added a solution of sodium hydroxide (47.3 g, 1.18 mol) in water (140 mL). The reaction was heated to 100° C. for 10 hours, then cooled to room temperature and diluted with H$_2$O (350 mL). The resulting slurry was stirred for 60 minutes, then the solids were filtered, washed with water and triturated with MeOH. The solids were dried under vacuum at 45° C. to give the title compound as a brown solid (22 g, 81.3%). $^1$H NMR (300 MHz, DMSO-d$_6$, 2.50 ppm): δ 11.77 (s, 1H), 8.51 (s, 1H), 8.21 (s, 1H), 7.74 (d, J=8.6 Hz, 2H), 7.53 (s, 1H), 7.52 (d, J=8.3 Hz, 2H), 6.51 (s, 1H). 13C NMR (75 MHz, DMSO-d$_6$, 40.0 ppm): δ 148.61, 141.79, 138.43, 132.15, 129.31, 129.01, 127.56, 127.28, 126.53, 120.09, 100.65.

Example 18. Preparation of 5-(4-chlorophenyl)-1H-pyrrolo[2,3-b]pyridine

To a round-bottomed flask equipped with mechanical stirrer, reflux condenser & nitrogen inlet was loaded 5-(4-chlorophenyl)-1H-pyrrolo[2,3-b]pyridine-3-carboxylic acid hydrobromide salt (50 g, 141 mmol), water (100 mL), DMSO (200 mL) and 48 w-% NaOH-solution (100 mL). The mixture was heated at temperatures between 113-115° C. for 24 hours. Water (100 mL) was added to the reaction and the mixture was allowed to cool at room temperature during two hours. The mixture was further cooled to 0° C. and kept at that temperature for one hour. The product was filtered and washed with water (100 mL) and MeOH (2×50 mL). After drying in vacuum oven at 50° C. for 16 hours 31.8 g (98%) of the title product was obtained. $^1$H NMR (300 MHz, DMSO-d$_6$, 2.50 ppm): δ 11.77 (s, 1H), 8.51 (s, 1H), 8.21 (s, 1H), 7.74 (d, J=8.6 Hz, 2H), 7.53 (s, 1H), 7.52 (d, J=8.3 Hz, 2H), 6.51 (s, 1H). $^{13}$C NMR (75 MHz, DMSO-d$_6$, 40.0 ppm): δ 148.61, 141.79, 138.43, 132.15, 129.31, 129.01, 127.56, 127.28, 126.53, 120.09, 100.65.

Example 19. Preparation of N-(3-(5-(4-chlorophenyl)-1H-pyrrolo[2,3-b]pyridine-3-carbonyl)-2,4-difluorophenyl)propane-1-sulfonamide (vemurafenib)

To a dry 500 mL flask equipped with a mechanical stirrer and a nitrogen inlet was added CH$_2$Cl$_2$ (70 mL), followed by 2,6-difluoro-3-(propylsulfonamido)benzoic acid (10.25 g, 0.037 mol). To the resulting solution was added oxalyl chloride (6.6 g, 0.052 mol) dropwise at room temperature, and the mixture was stirred for 2 hours. The mixture was concentrated in a rotavapor at 30° C. to remove excess oxalyl chloride, then redissolved in CH$_2$Cl$_2$ (70 mL). To a second 100 mL flask similarly equipped was loaded dichloromethane (70 mL) followed by 5-(4-chlorophenyl)-1H-pyrrolo[2,3-b]pyridine (7.0 g, 0.031 mol). The mixture was cooled to 0-5° C., and anhydrous AlCl$_3$ (16.3 g, 0.12 mol) was added portionwise. After the addition was complete, this mixture was added to the previously prepared acid chloride solution at room temperature and stirred for 5 hours. Upon completion the reaction was quenched with H$_2$O (80 mL) and stirred for 1 hour. The solids were filtered and dried under vacuum to give vemurafenib as an off-white solid (10.5 g, 70%). $^1$H NMR (400 MHz, DMSO-d6, 2.50 ppm): δ 13.04 (1H, s), 9.79 (1H, s), 8.71 (1H, s), 8.65 (1H, s), 8.26 (1H, s), 7.78 (2H, d, J=8.4 Hz), 7.63-7.58 (1H, m), 7.56 (2H, d, J=8.4 Hz), 7.31-7.26 (1H, app. Triplet), 3.15-3.11 (2H, m), 1.80-1.68 (2H, m), 0.96 (3H, t, J=7.4 Hz). $^{13}$C NMR (100 MHz, DMSO-d6, 40 ppm): δ 181.13, 156.52 (dd, J$_{C-F}$=246.2, 6.9 Hz), 152.83 (dd, J$_{C-F}$=249.6, 8.8 Hz), 149.50, 144.42, 139.42, 137.50, 133.01, 130.75, 129.56, 129.39, 129.35-129.20 (m), 127.58. 122.43 (dd, $J_{C-F}$=13.5, 3.5 Hz), 118.64 (dd, $J_{C-F}$=24.4, 22.5 Hz), 117.98, 116.20, 112.83 (dd, $J_{C-F}$=22.6, 3.4 Hz), 53.97, 17.33, 13.09.

The invention claimed is:

1. A process for manufacture of a compound of formula (I):

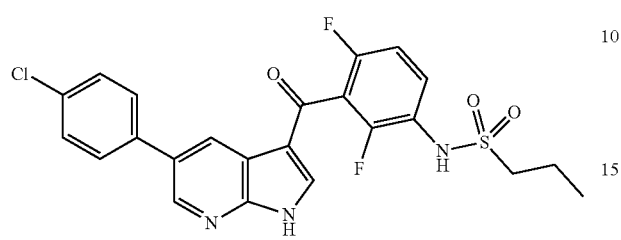

which process comprises:
a) reacting a compound of formula (III):

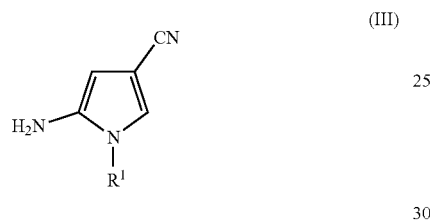

wherein $R^1$ is $C_{1-5}$ alkyl, $C_{3-6}$ cycloalkyl, $C_{3-5}$ alkenyl or optionally substituted benzyl, or sulfonyl, or carbonyl with either a compound of formula (IV); or a compound of formula (VI):

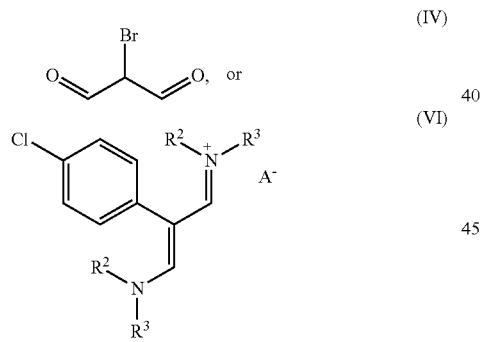

wherein $R^2$ and $R^3$ are groups suitable for formation of a Vilsmeier reagent and $A^-$ is a suitable non-coordinating anion, to produce a compound of formula (IX) having a nitrile group:

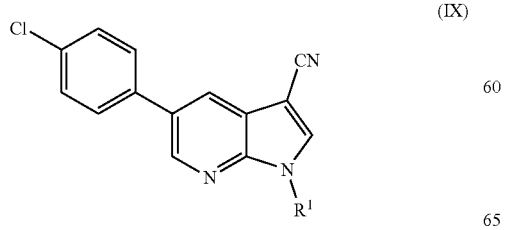

wherein $R^1$ is as defined herein; and b) subjecting the compound of formula (IX) to removal of the $R^1$ group and converting the nitrile group to a carboxylic acid, and performing a decarboxylation to produce a compound of formula (X):

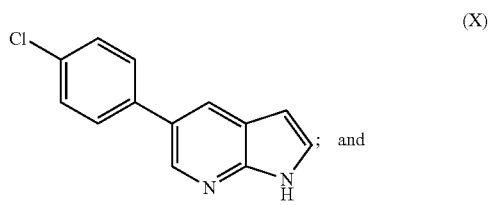 [SMILES: Clc1ccc(-c2cnc3[nH]ccc3c2)cc1]

c) reacting the compound of formula (X) with 2,6-difluoro-3-(propylsulfonamido)benzoic acid to give a compound of formula (I).

2. A process according to claim 1, wherein
a) the compound of formula (III):

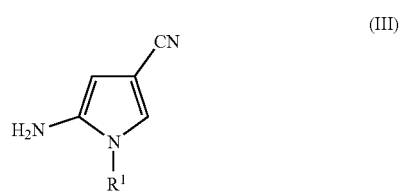

wherein $R^1$ is $C_{1-5}$ alkyl, $C_{3-6}$ cycloalkyl or optionally substituted benzyl, is reacted with the compound of formula (IV):

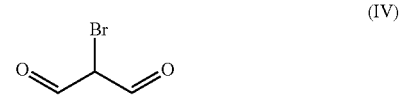

to obtain compound of formula (VII):

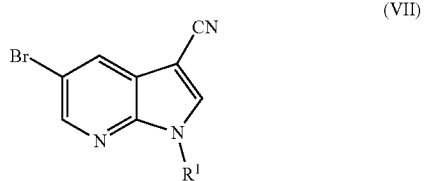

wherein $R^1$ is as defined herein; and
b) subsequently reacting the compound of formula (VII) in a presence of a palladium catalyst with a compound of formula (VIII):

to produce the compound of formula (IX):

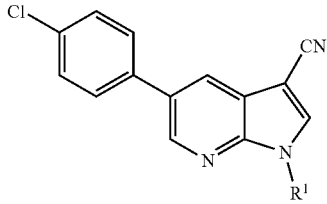
(IX)

wherein R¹ is as defined herein; and
a) subjecting the compound of formula (IX) to removal of the R¹ group and converting the nitrile group to a carboxylic acid, and performing a decarboxylation to produce the compound of formula (X):

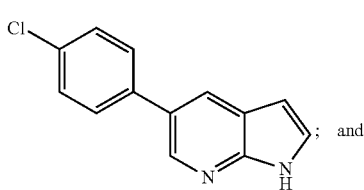
(X) ; and d) reacting the compound of formula (X) with 2,6-difluoro-3-(propylsulfonamido)benzoic acid to give a compound of formula (I).

3. A process according to claim 1, wherein
a) the compound of formula (III):

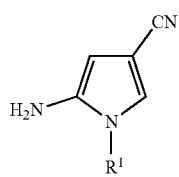
(III)

wherein R¹ is $C_{1-5}$ alkyl, $C_{3-6}$ cycloalkyl or optionally substituted benzyl, is reacted with the compound of formula (VI):

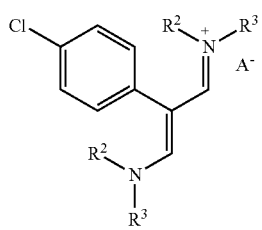
(VI)

wherein R² and R³ are groups suitable for formation of a Vilsmeier reagent and A⁻ is a suitable non-coordinating anion, to produce the compound of formula (IX):

(IX)

wherein R¹ is as defined herein; and
b) subjecting the compound of formula (IX) to removal of the R¹ group and converting the nitrile group to a carboxylic acid, and performing a decarboxylation to produce the compound of formula (X):

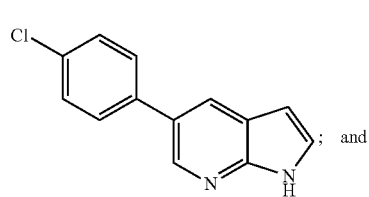
(X)

; and c) reacting the compound of formula (X) with 2,6-difluoro-3-(propylsulfonamido)benzoic acid to give a compound of formula (I).

4. A process according to claim 2, wherein said process is carried out in a presence of a catalyst selected from the group consisting of Pd(PPh₃)₄, Pd(dba)₂, Pd₂(dba)₃, Pd(dppf)Cl₂·CH₂Cl₂, (PPh₃)₂PdCl₂, Pd(OAc)₂, PdCl₂ or in combination with phosphine ligands, PPh₃, P(o-tol)₃, dppf, dppp, dppe, dppb, PCy₃, P(n-Bu)₃, P(t-Bu)₃, XantPhos, DPEPhos, rac-BINAP, or rac-SEGPHOS.

5. A process according to claim 1, wherein R² and R³, independently, are methyl, ethyl, isopropyl, or together with nitrogen atoms to which they are attached form a piperidine ring.

6. A process according to claim 5, wherein R² and R³ are methyl.

7. A process according to claim 1, wherein A⁻ is the anion of an alkali metal salt selected from the group consisting of NaPF₆, KPF₆, KBF₄, NaBF₄, NaClO₄, and KClO₄.

8. A process according to claim 1, comprising:
preparing the compound of formula (III):

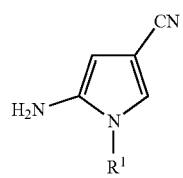
(III)

by reacting a compound of formula:

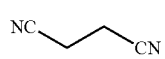
(II)

with ethyl formate and a compound of formula R¹—NH₂, wherein R¹ is $C_{1-5}$ alkyl, $C_{3-6}$ cycloalkyl or optionally substituted benzyl.

9. A process according to claim 8, wherein $R^1$ is $C_{1-5}$ alkyl.

10. A process according to claim 9, wherein $R^1$ is a t-butyl group.

11. A process according to claim 1, comprising:
preparing the compound of formula (VI):

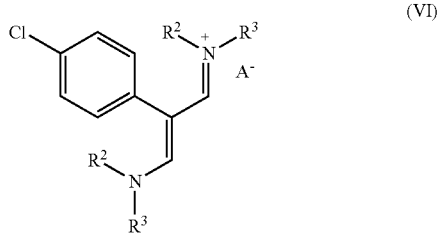

by reacting a compound of formula (V):

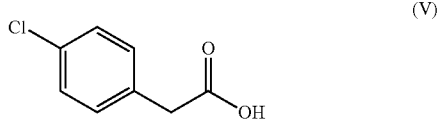 [SMILES: O=C(O)Cc1ccc(Cl)cc1]

with a compound of formula $R^2R^3NCHO$, wherein $R^2$ and $R^3$, independently, are methyl, ethyl, isopropyl, or together with the nitrogen atoms to which they are attached form a piperidine ring.

12. A process according to claim 11, wherein $R^2$ and $R^3$ are methyl.

13. A process according to claim 10, comprising:
removal of the t-butyl group in a presence of aluminum thrichloride ($AlCl_3$) or with 95-100 w-% sulfuric acid.

14. A process according to claim 1, comprising:
converting the nitrile group of the compound of formula (IX) to the carboxylic acid using hydrochloric, hydrobromic or sulfuric acid.

15. A process according to claim 1, wherein the decarboxylation is a base catalysed decarboxylation.

16. A process according to claim 15, comprising:
performing the base catalysed decarboxylation using sodium hydroxide.

17. A process according to claim 3, wherein $R^2$ and $R^3$, independently, are methyl, ethyl, isopropyl, or together with nitrogen atoms to which they are attached form a piperidine ring.

18. A process according to claim 3, wherein $A^-$ is the anion of an alkali metal salt selected from the group consisting of $NaPF_6$, $KPF_6$, $KBF_4$, $NaBF_4$, $NaClO_4$, and $KClO_4$.

19. A process according to claim 2, comprising:
preparing the compound of formula (III):

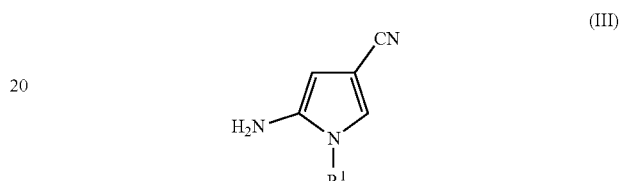

by reacting a compound of formula:

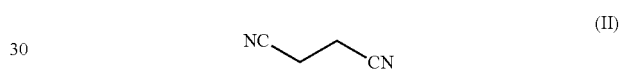

with ethyl formate and a compound of formula $R^1$—$NH_2$, wherein $R^1$ is $C_{1-5}$ alkyl, $C_{3-6}$ cycloalkyl or optionally substituted benzyl.

20. A process according to claim 2, comprising:
converting the nitrile group of the compound of formula (IX) to the carboxylic acid using hydrochloric, hydrobromic or sulfuric acid.

* * * * *